United States Patent [19]

Nomoto et al.

[11] 4,437,465

[45] Mar. 20, 1984

[54] MEDICAL TREATMENT SEWING MACHINE

[75] Inventors: Reishi Nomoto, Kanagawa; Masahiro Akimoto, Hino; Masayoshi Takahashi, Sagamihara, all of Japan

[73] Assignee: Janome Sewing Machine Co., Ltd., Tokyo, Japan

[21] Appl. No.: 344,774

[22] Filed: Feb. 1, 1982

Related U.S. Application Data

[63] Continuation of Ser. No. 148,595, May 12, 1980, abandoned.

[30] Foreign Application Priority Data

May 17, 1979 [JP] Japan .................................. 54-60642

[51] Int. Cl.³ ............................................. A61B 17/06
[52] U.S. Cl. ...................................... 128/340; 112/161; 112/276
[58] Field of Search ................ 128/329, 340; 112/169, 112/276

[56] References Cited

U.S. PATENT DOCUMENTS

2,327,353  8/1943  Karle .................................. 128/340

FOREIGN PATENT DOCUMENTS

2081099  4/1981  United Kingdom ................ 128/340

Primary Examiner—Robert Peshock
Attorney, Agent, or Firm—Michael J. Striker

[57] ABSTRACT

A suturing instrument for a surgical operation includes a suturing portion having a base, a vertically reciprocating needle holder carrying a needle with an upper thread, a device for supplying a predetermined amount of the upper thread to the needle and a loop taker supported in the base for turnable movement relative thereto and operative for catching a thread loop formed on the needle. The device for supplying the upper thread, the loop taker and the needle holder are activated for sequential operation by a control portion of the instrument which includes a fluid drive device connected to the suturing portion and including a plurality of hydraulic cylinders. The control portion is activated by a manually operated switch which actuates an electric circuit and a switching device operating a plurality of the cylinders for sequentially imparting the reciprocating movements to the needle, the loop taker and the thread supplying device.

6 Claims, 48 Drawing Figures

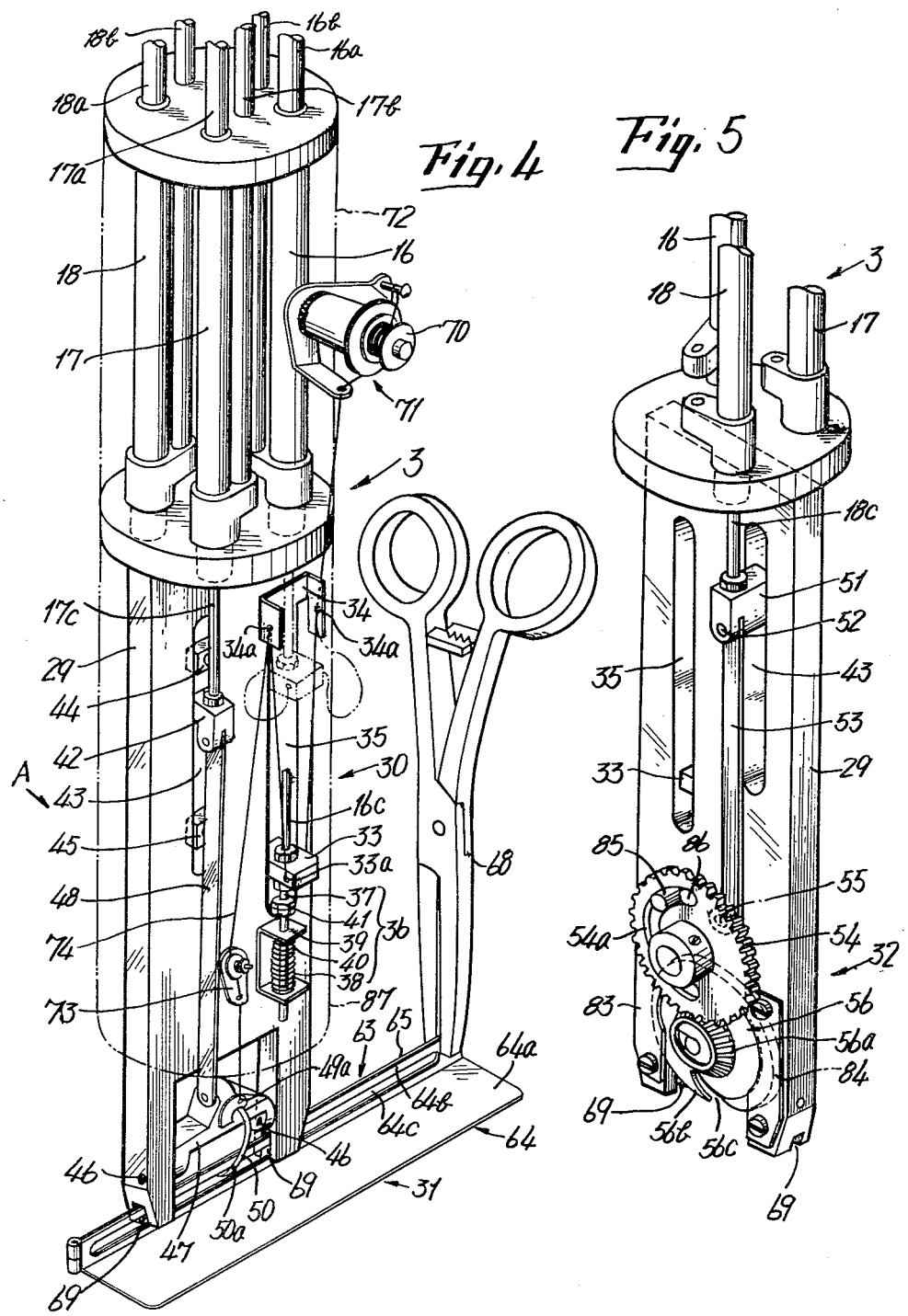

Fig. 4-a
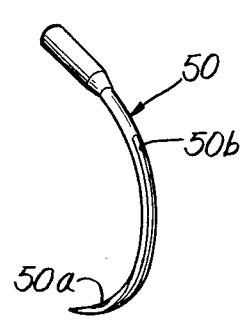
Fig. 4-b
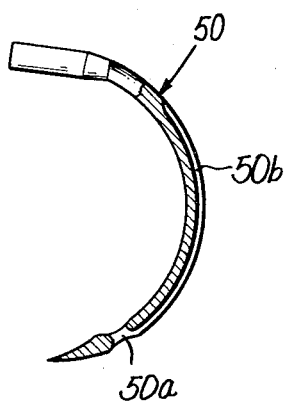
Fig. 4-c
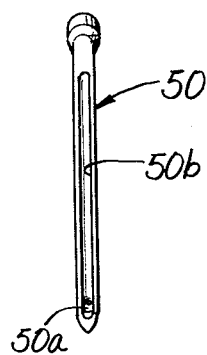
Fig. 4-d
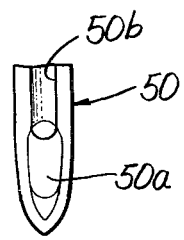

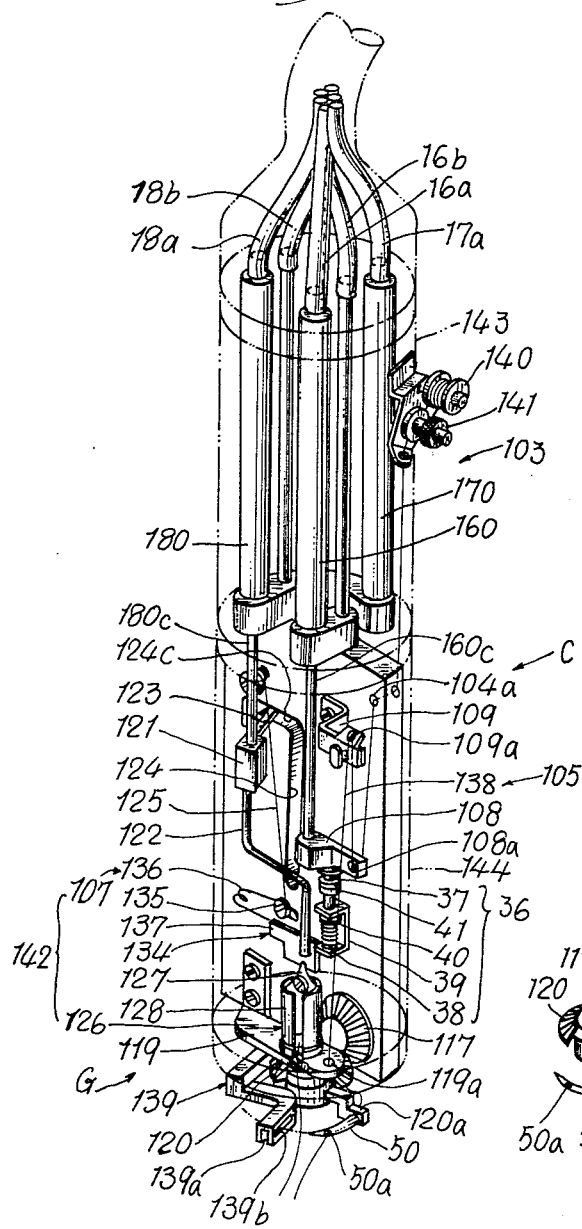
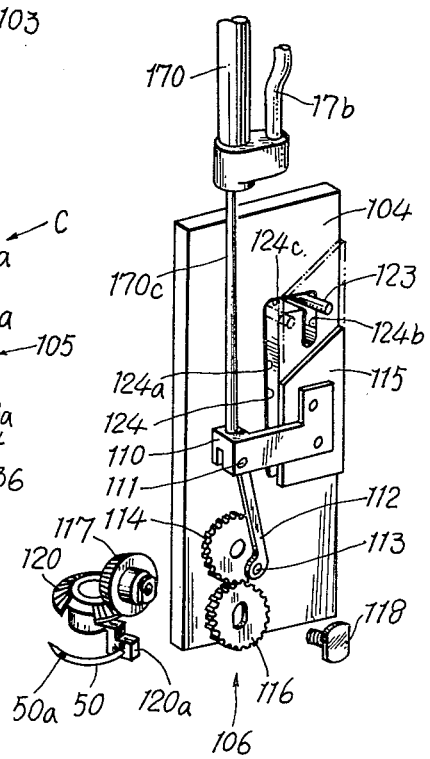

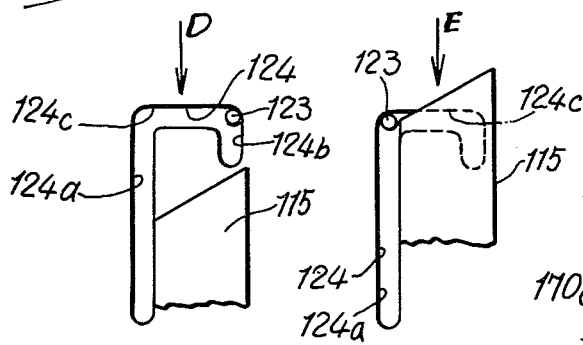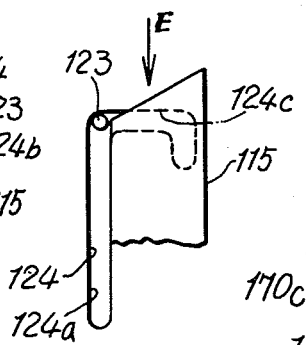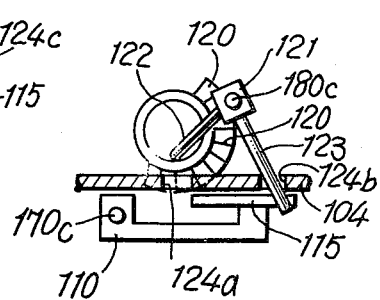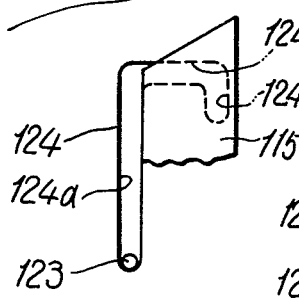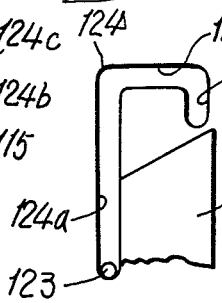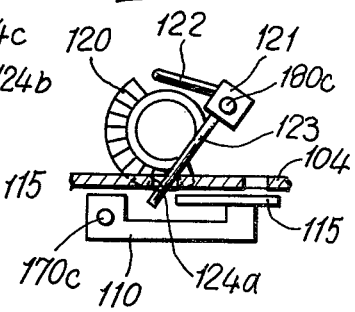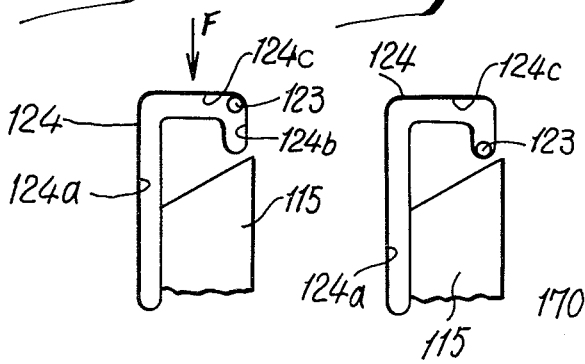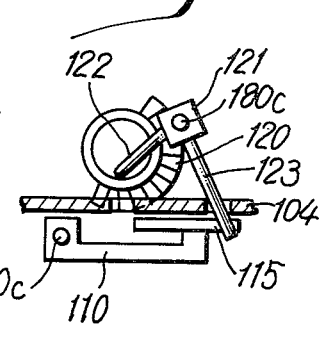

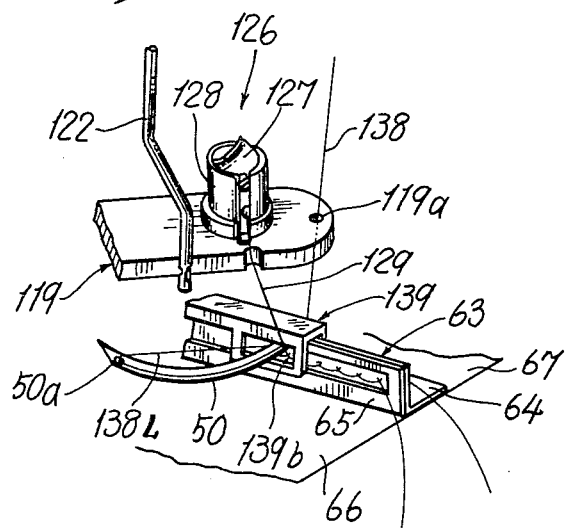
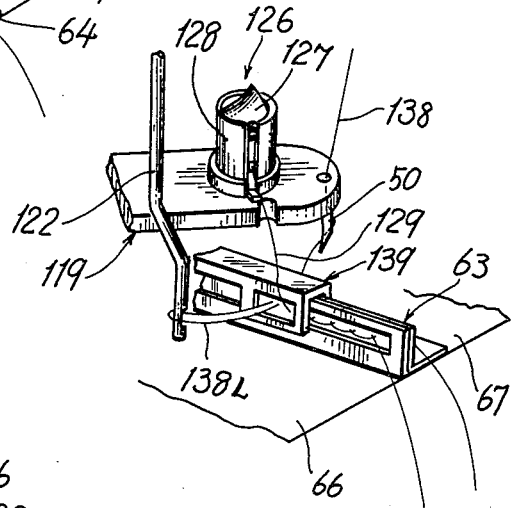
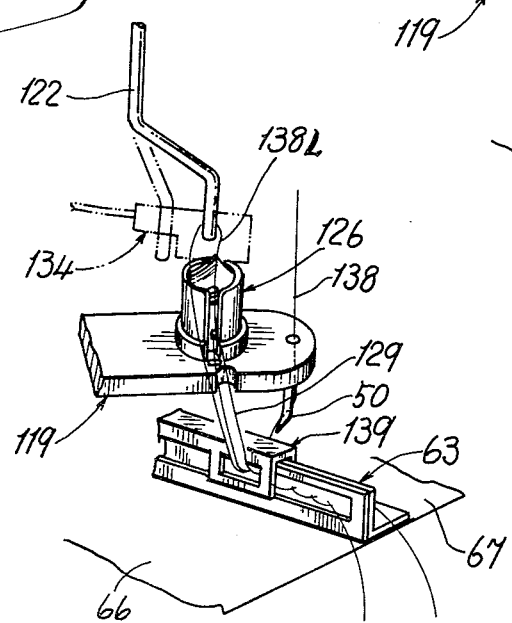

MEDICAL TREATMENT SEWING MACHINE

This is a continuation, of application Ser. No. 148,595, filed May 12, 1980 and now abandoned.

BACKGROUND OF THE INVENTION

The invention relates to a sewing machine for medical treatments, and more particularly to a sewing machine used in the surgical operation to suture up the skins or the dura mater in the craniotomy, thereby to heighten the efficiency of surgical operations and also to improve the suturing up seams.

The craniotomy for curing the hydrocephalus, cerebral internal hemorrhage and others is operated in order of (1) incising the skin, (2) making holes in the head skull, (3) cutting between the holes to make a window, and (4) incising the dura mater.

The craniotomy has recently been performed in short period of time by means of a developed electrical drill or a high-speed drill of the gas turbine. On the other hand, when recovering the head in the reverse order to the above, the conventional way for knotting the incised dura mater is to use a curved needle with a silk thread in a needle eye by hand and the needle is inserted through the part to be sutured, and the thread is combined per stitch. Therefore, it takes 30 to 60 minutes to suture up the dura mater only, thus imposing a physical burden to the patient as well as the operator.

Another conventional way is to combine the incised dura mater by means of the metallic clips such as silver. According to this method, the combination of the dura mater is completed in a shorter time. However, so many metallic clips remain in the head. These clips make unclear the images of X-rays or the computer-tomograph when the process after the operation is observed.

SUMMARY OF THE INVENTION

The present invention has been devised to eliminate the shortcomings of the prior art, and objects of the invention are as follows:

It is a primary object of the invention to provide a medical sewing machine which enables to exactly and successively suture up the incised parts of human body with the silk thread or nylon thread to speed up the surgical operation.

It is another object of the invention to provide a medical sewing machine which is structurally compact effectively operated.

It is another object of the invention to provide a medical sewing machine which is connected to a control part by flexible tubes, so that the sewing machine may be freely handled.

It is another object of the invention to provide a small sized medical sewing machine which is disconnected from the control part, and is partly disassembled to be washed as well as disinfected after surgical operation.

It is another object of the invention to provide a medical sewing machine which is easily adjusted to provide a desired length of stitches.

It is still another object of the invention to provide a medical sewing machine which is driven by a controlled fluid without a sound giving an undesirable influence to the patient.

The other features and advantages of the invention will be apparent from the following description of the invention in reference to preferred embodiments as shown in the attached drawings.

BRIEF DESCRIPTION OF THE DRAWINGS

FIG. 1 to FIG. 19 show a first embodiment of the invention, and

FIG. 1 is a perspective view of an outer appearance of a medical treating sewing machine, FIG. 2 is air-pressure circuit diagram, FIG. 3 is a block diagram of an electric circuit, FIG. 4 is a perspective view of a suturing part of the sewing machine, FIG. 4-a is an enlarged view of a curved needle, FIG. 4-b is a cross sectional view of the above, FIG. 4-c is a front view of the above, FIG. 4-d is a further enlarged view of an end point thereof, FIG. 5 is a perspective view seen from "A" arrow in FIG. 4.

FIG. 6 is a perspective view of a thread take up lever

FIG. 7 is perspective views of a lower thread bobbin and a bobbin case.

FIG. 8 is a cross sectional view of the thread take up lever.

FIG. 9 is a perspective view of a presser,

FIG. 10 is a cross sectional view showing keeping dura maters with the presser,

FIG. 11 is a sequence of solenoid,

FIG. 12 is sequences of each of mechanisms of a suturing part,

FIG. 13 is a cross sectional view showing a suturing process by the suturing part, FIG. 14 to FIG. 19 are views showing actuations at suturing operation of main part of a thread take up lever mechanism seen from "B" arrow in FIG. 13, FIG. 20 to FIG. 44 show a second embodiment of the invention, FIG. 22 is a perspective view of a suturing part of the sewing machine, FIG. 23 is a perspective view of disembling the main part seen from "C" arrow in FIG. 22, FIG. 24 and FIG. 25 show relation between a shape of an end point of a looper and a thread loop, FIG. 30 to FIG. 38 are views showing actuations of the looper at suturing operation, FIG. 31 is a view seen from "D" arrow in FIG. 30, FIG. 33 is a view seen from "E" arrow in FIG. 32, FIG. 37 is a view seen from "E" arrow in FIG. 36, and FIG. 38 to FIG. 44 are views showing actuations at suturing operation of the looper mechanism and the shuttle mechanism, seen from "G" arrow in FIG. 22.

DETAILED DESCRIPTION OF THE INVENTION

Figure 1:
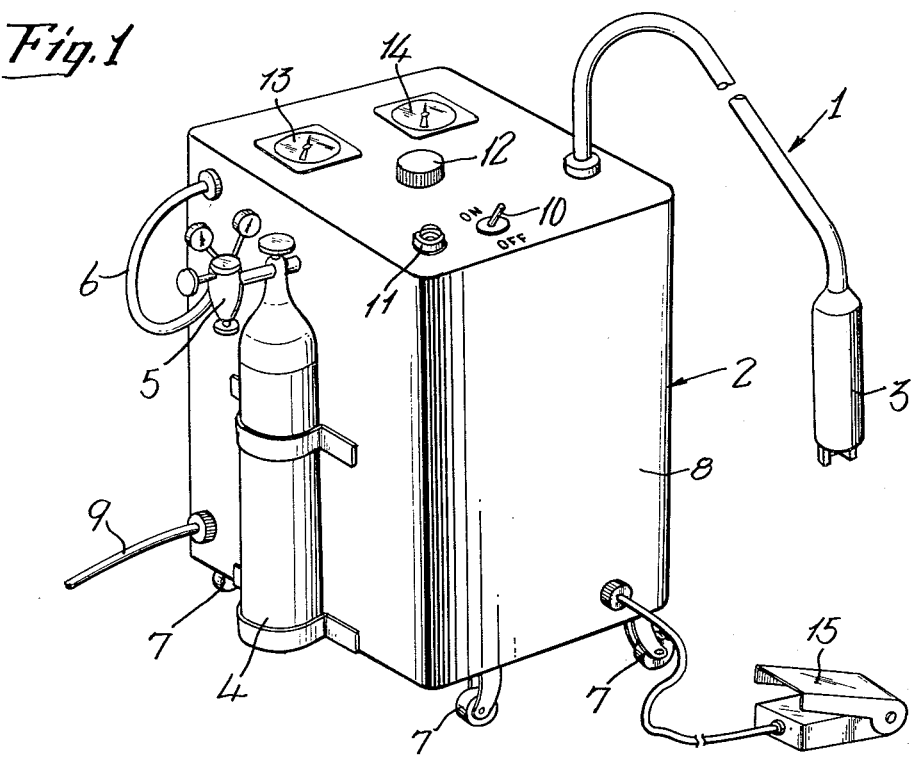

The invention will be explained in reference to the attached drawings. In FIG. 1, the numeral 1 denotes a sewing machine device for medical treatments composed of a control part 2 and a suturing part 3. The numeral 4 shows a high pressure bomb containing $N_2$- gas as a driving source of the suturing part 3. The pressure of the fluid is primary-reduced by a primary regulator 5. The numeral 6 is a pressure resistant hose connecting the bomb 4 to an air pressure circuit within the control part 2. The control part 2 is substantially composed of an electric circuit and the air pressure circuit, and is housed in a box 8 having a plurality of casters 7. The numeral 9 is a code connected to a power source. 10 is a switch, and 11 is an indicating lamp of the power source. 12 is a control dial of a secondary regulator (not shown). 13 and 14 are pressure gauges, the former showing the pressure of the primary side and the latter showing the pressure of the secondary side. 15 is a foot controlled switch of ON-OFF type for giving a suturing order to the sewing machine.

Figure 2:
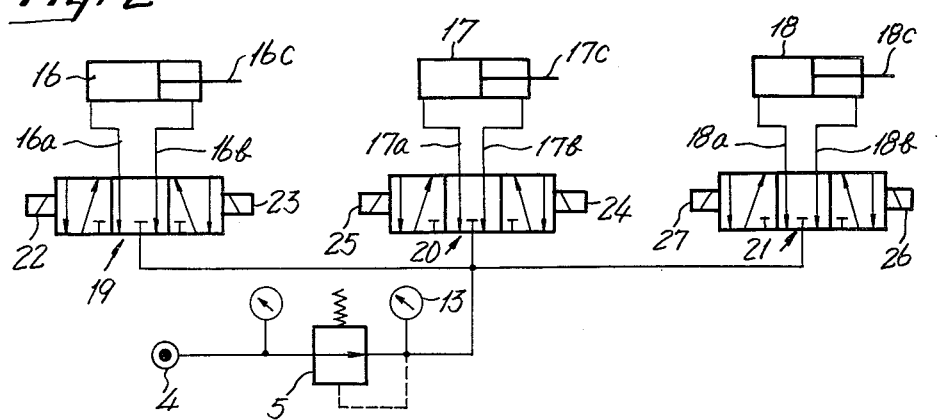

In reference to FIG. 2, the numerals 16, 17 and 18 are cylinders to be operated by the pressed fluid. These cylinders are connected in this sequence to the high pressure bomb 4 of $N_2$-gas via solenoid type switching valves 19, 20 and 21 and the regulator 5. The numerals 22 to 27 are solenoids of the switching valves 19 to 21.

Figure 3:
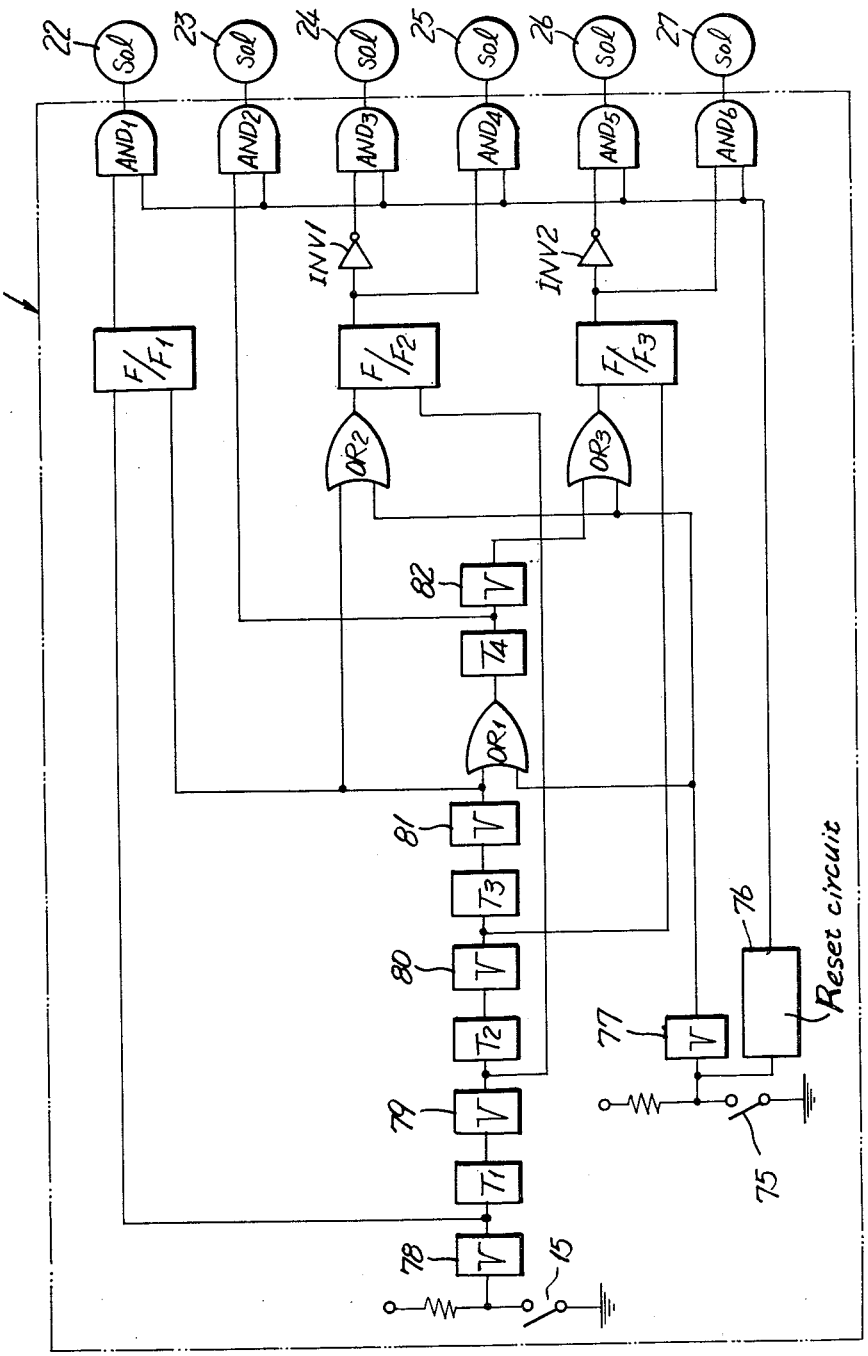

In reference to FIG. 3, the numeral 28 is a block diagram of the electric control circuit for sequentially controlling the solenoids 22 to 27, details of which will be explained herein later in connection to the operation thereof.

In reference to FIGS. 4 and 5 showing the suturing part 3. namely, a sewing machine part of the invention, the cylinders 16, 17 and 18 are vertically arranged on the upper part of an elongated base 29 of a thread take-up mechanism 30, to drive a needle mechanism 31 and a loop taker mechanism 32 respectively. These cylinders are connected to the solenoid type switching valves 19 to 21 within the box 8 through a plurality of the flexible tubes 16a, 16b to 18a, 18b. These flexible tubes 16a to 18b may be taken off from the tops of the cylinders 16 to 18 when it seams necessary.

The cylinder 16 is provided with a vertically extending cylinder rod 16c which has a thread take-up element 33 secured to the lower end thereof. The thread take up element 33 is vertically moved, as the cylinder rod 16c is moved, in a vertical guide groove 35 formed in the base 29 and between two thread guiding holes 34a of a thread guide 34 secured to the support 29. The thread take-up element 33 and the thread guide 34 constitute a thread take-up mechanism 30. At the lower end of the stroke the thread take-up lever 33 contacts the upper end of a pin 37 of a feed regulator 36 for determining a stitch length, and compresses a spring 38. The pin 37 is inserted, for vertical movement, in a U-shape support element 39 and is normally maintained at a position in which a stopper 40 of the pin 37 is pressed against the upper face of the support element 39 by the compression spring 38 in the support element. If the pin 37 is pushed downwardly, the pin is moved against the action of the compression spring 38 until a stopper nut 41 of the pin 37 contacts the upper face of the support element 39. Since the biassing force of the spring 38 is determined to be weaker than the actuating force of the cylinder 16, but stronger than the total of the friction resisting force of the cylinder rod 16c and a sealing material and the weight of said cylinder rod itself, the pin 37 is depressed down if the pressure fluid acts on the cylinder 16, and the pin 37 is pushed up to the initial position if action of the pressure fluid is eliminated. In this regard, the moving amount of the pin 37 may be adjusted by changing the position of the nut 41.

A cylinder rod 17c of the cylinder 17 has a juncture element 42 secured to the lower end thereof. As the rod 17c is vertically moved, the element 42 is moved in a vertical guide groove 43 of the base 29 on one side thereof. The moving range of the juncture element 42 is limited by an upper stopper 44 and a lower stopper 45 adjustably arranged on the base 29. The base 29 is fork shaped at its lower end thereof. In the forked end of the base, a needle holder 47 is pivoted by a pair of pins 46. The needle holder 47 is connected to the juncture element 42 by a link 48. The needle holder 47 has a thread guide 49 and a curved needle each secured thereto. The curved needle 50 has a needle hole 50a formed at the point thereof and a groove 50b formed along the outer periphery thereof. The thread guide 49 has a thread guiding hole 49a which is positioned adjacent to the needle 50 and is in a plane where the groove 50b is located, so as to guide the thread into the groove 50b of the curved needle 50.

In reference to FIG. 5, a cylinder rod 18c of the cylinder 18 has a juncture element 51 secured to the lower end thereof. The juncture element 51 is vertically moved in the groove 43 on the other side of the base 29. A transmission link 53 is at the upper end connected to the juncture element 51 by a pin 52, and is at the lower end connected to a gear 54 by a pin 55. The gear 54 is rotatably mounted on the base 29. As shown, the gear 54 is formed with a semicircular groove 54a, in which pins 85, 86 on the base 29 are inserted to limit the rotational movement of the gear 54. The gear 54 is in mesh with a gear 56a of a loop taker 56 which is rotatably positioned in a race 84 formed on the base 29 and is held there by a holding plate 83.

Figure 6:
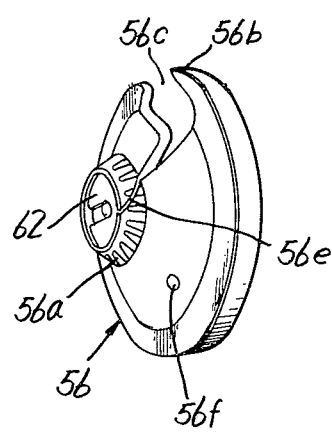
Figure 7:
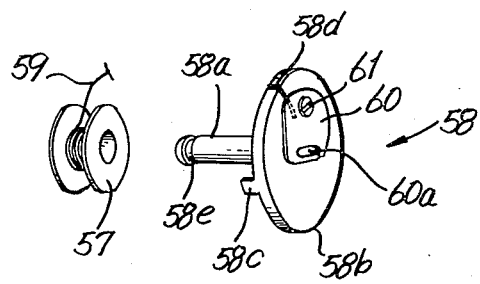
Figure 8:
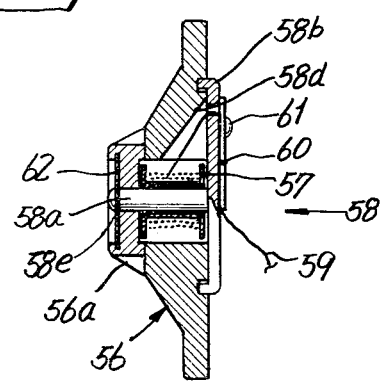

In reference to FIG. 6 to FIG. 8, the loop taker 56 is cone shaped, and is provided at its top with the gear 56a, and a hook 56b for catching the thread on the outer periphery thereof. Further, the loop taker 56 is formed with a cutout 56c as shown. The loop taker 56 is, on the rear side, formed with a chamber 56d to receive a lower thread bobbin 57, and the gear 56a is formed with a thread guiding groove 56e about 0.5 to 1 mm deeper than the bottom of the gear, the groove 56e being continued to the cutout 56c in a smooth curve. The numeral 58 denotes a bobbin carrier composed of a bobbin supporting shaft 58a and a disk 58b. The disk 58b is formed with a peripheral plange 58b with a projection 58c inserted into a hole 56f of the loop taker 56 to position the bobbin carrier 58 relative to the former. As shown, a thread guide groove 58d is provided in the periphery of the disk 58b, and a plate spring 60 is attached to the rear side of the disk 58b by a screw 61 to give a tension to the lower thread 59. The bobbin carrier 58, together with the lower thread bobbin 57, is mounted to the loop taker 56 in such a manner that the projection 58c is inserted into the positioning hole 56f of the loop taker, and a groove 58e of the bobbin supporting shaft 58a is in engagement with a snap spring 58e of the loop taker 56, as shown in FIG. 8. The lower thread outlet 60a of the plate spring 60 is positioned near the rotation center of the bobbin carrier disk 58b so as to minimize the movement of the lower thread 59 during rotation of the disk 58b. Since the loop taker 56 is rocking, twisting of the lower thread 59 is not accumulated even if the bobbin carrier 58 is turned with the loop taker.

Figure 9:
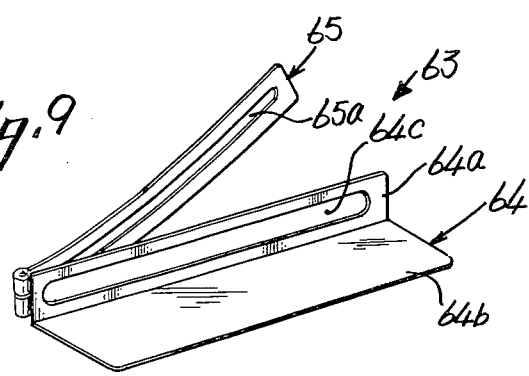

In reference to FIG. 4 and FIG. 9, the numeral 63 denotes a presser foot for the dura mater to be sewn up, which is of L-shape in cross section and is composed of a vertical pressing part 64a and a lateral plain part 64b and another vertical presser plate 65 slightly curved in the inward direction and hinged to the pressing part 64a. As shown, the pressing parts 64a and 65 are formed with laterally elongated slots 64c, 65a respectively which are in alignment when these parts meet each other.

Figure 10:
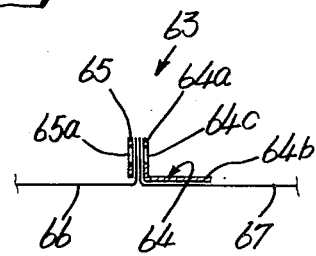

In reference to FIG. 10, two sheets of the dura meters 66, 67 are, at suturing, held together by the pressing parts 64a, 65, and fixed, in a condition that the free ends of pressing parts 64a, 65 are clamped by a forceps 68 (see FIG. 4), and in this case, the curve of the presser plate 65 is effective to securely hold the dura maters 66, 67. Further, it also brings about the same effect to form a plurality of concaves and convexs on the presser faces, which engage each other at holding the dura maters 66, 67, or to provide, instead of the concaves and the convexs, a plurality of needles and small holes at positions corresponding to the needles. The presser foot 63 may be changeable in dependence on the parts or sizes to be sewn up. The numerals 69 are guide grooves (see FIG. 5) formed at the lower forked ends of the base 29 to engage the vertical pressing parts 64a, 65 of the presser foot 63.

In FIG. 4 the numeral 70 denotes an upper thread bobbin and 71 is a thread tension each mounted on an upper cover 72 which is detachably attached to the base 29. A lower cover 87 is also detachably attached to the base. The numeral 73 is a thread tension mechanism provided between the thread take-up mechanism 30 and the needle mechanism 31 and gives to the upper thread 74a weak tension of about several grams.

A next reference will be made to the operation of the first embodiment of the invention constructed as mentioned above. Prior to starting a suturing operation, the dura mater is set to the presser 63. The presser is appropriately selected from the prepared ones which are different in size and shape in dependence upon the situations, and the two sheets of the dura maters 66, 67 are, as shown in FIG. 10, held up by the presser 63 at the both sides, and the free end of the presser is fixed by the forceps 68 (see FIG. 4), so that the needle may easily penetrate into the dura maters to be sewn up and the suturing may be exactly carried out. In this case, the suturing part is easily reached by guiding the sewing machine 3 along the presser foot 63, and the remaining parts are completely protected from the operating influence of the sewing machine mechanism. Suturing up of the dura maters 66, 67 (FIG. 10) is started by engaging the forked ends of the base 29 to the vertical pressing parts 64a, 65 of the presser foot 63 as shown in FIG. 4. The suturing seams are each formed by operating the foot switch 15. Namely the sewing machine 3 is operated to form a seam by one operation of the foot switch 15, and is stopped until the foot switch 15 is operated again after it is released. While the sewing machine 3 is inoperative, the machine is displaced to form the next seam. The manually displaced amount of the machine 3 determines the length of a seam.

The lower cover 87 is easily removed from the base 29 by loosening the fixing elements such as screws. The upper thread is passed, from the upper thread bobbin 70, through the thread tension 71, the thread guide 34 and the take-up element 33 and is passed again through the thread guide 34, and then is guided to the thread tension 73 where the thread is properly tensed, and then passed through the thread guide 49. Finally the thread 74 is guided into the eye 50a of the curved needle 50 along the outer peripheral groove 50b thereof.

Figure 11:
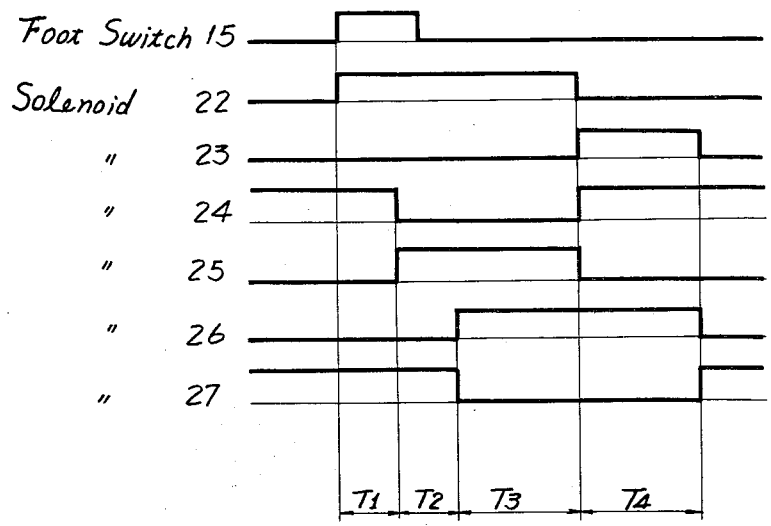
Figure 12:
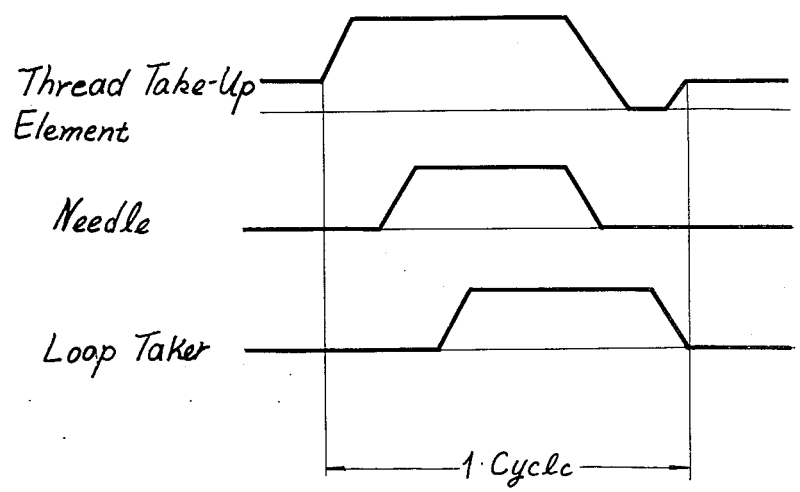

The seams are formed up by actuating the mechanisms of the sewing machine in the sequence as shown in FIG. 12. These respective mechanisms are, as shown in FIG. 11, actuated by the solenoids 22 to 27 of the switching valves 19 to 21 which are sequentially controlled in an electric circuit.

An explanation will be made to the sequential control of the solenoids 22 to 27 by the electric circuit in reference to the block diagram of the circuit shown in FIG. 3. When a power source switch (not shown) is made ON and subsequentlly a reset switch 75 is made ON, the control circuit is set to an initial condition. Namely when the power source switch is set ON, flip-flop circuits (F/F1) to (F/F3) and a reset circuit 76 become a non-output condition (the output condition is "1", and a non-output condition is "0") due to the circuit constants. In this condition, the solenoids 22 to 27 are made OFF. Subsequently, when a reset switch 75 is made ON for a short period of time, the output of the reset circuit 76 is "1" and the inputs of one sides of AND circuits AND1 to AND6 are made "1". On the other hand, due to a falling signal of the reset switch 75, a trigger circuit 77 gives a pulse signal to OR circuits OR1 to OR3, thereby to activate a timer circuit T4 through the OR circuit OR1. The solenoid 23 is, therefore, made ON for only a period of T4 time. Simultaneously, the outputs of the OR2 and OR3 cause the outputs F/F2 and F/F3 to produce a signal "1" one after another to make ON the solenoid 25, 27 are made ON, and OFF condition is maintained of the solenoids 24 and 25 which are connected to the F/F2 and F/F3 via inverter circuits INV1 and INV2 as well as AND3 and AND5. Thus, the solenoids 22 to 27 and the cylinders 16 to 18 to be controlled by these solenoids are set to the initial condition. As apparent from the above explanation, in the initial condition of these cylinders 16 to 18, the cylinder rod 16c is center-opened (later mentioned) and the cylinder rods 17c, 18c are at the elevated positions.

In the initially set process, the solenoid 23 is once made ON and it is made OFF after T4 time, whereby the pressure fluid acts on the rod side of the cylinder 16 and the thread take-up element 33 in once lowered to push down the pin 37 of the feed regulator 36, thereby to compress the spring 38 by a predetermined amount. The solenoid 23 becomes OFF after the T4 time, whereby the change-over valve 19 controlling the cylinder 16 is center-opened. Therefore, the rod side of the cylinder 16 and the cylinder side become of a pressure equal to the atmospheric pressure, and the thread take-up element 33 is pushed up by the predetermined amount by the biassing force of the spring 33 against the weight of the cylinder rod 16c itself and the friction force thereof. Thus a predetermined amount of the upper thread 74 is supplied to the needle 50, and therefore the feeding amount of the sewing machine 3 is determined.

When the foot operated switch 15 is made ON, an output of F/F1 is "1" and the solenoid 22 is made ON due to a signal from a trigger circuit 78, and at the same time the timer circuit T1 is triggered and activated for a period of T1 time. A falling signal of the timer circuit T1 after the time T1 is converted into a pulse signal by a trigger circuit 79, thereby to actuate the timer circuit T2 for period of T2 time and to cause the flip-flop circuit F/F2 to produce the output "0" so that the solenoid 24 is made ON and the solenoid 25 is made OFF. Similarly after T2 time, the output of F/F3 is made "0" by a signal from the trigger circuit 80, and the solenoid 26 is made ON and the solenoid 27 is made OFF, and at the same time the timer circuit T3 is activated for a period of T3 time. Similarly after T3 time, the output of F/F1 is made "0" by a signal from a trigger circuit 81, and the solenoid 22 is made "OFF and the solenoid 23 is made ON, and since the output of F/F2 is made "1". Therefore, the solenoid 24 is made OFF and the solenoid 25 is mde ON and at the same time the timer circuit T4 is actuated for T4 time. After T4 time, the output of F/F3 is made "1" by the signal from the trigger circuit 82, and the solenoid 26 is made OFF and the solenoid 27 is made ON. In the above mentioned process, the control circuit has made one cycle of operation and returns to the initial condition. Subsequently, each time the foot switch 15 is operated the cycle of the above sequential control is repeated. By means of the solenoids 22 to 27 to be sequentially controlled as said, each of the mechanisms of the sewing machine connected to each of the cylinders 16 to 18 is operated as mentioned under to form the suturing seams.

Namely when the foot switch 15 is operated with the foot, the solenoid 22 is made ON and the $N_2$-gas flows into the rod side of the cylinder 16 via a switching valve 19 to elevate the take-up lever 33 up to a position shown by a phamton line in FIG. 4, thereby to give a sag to the thread 74 for one stitch.

Figure 13:
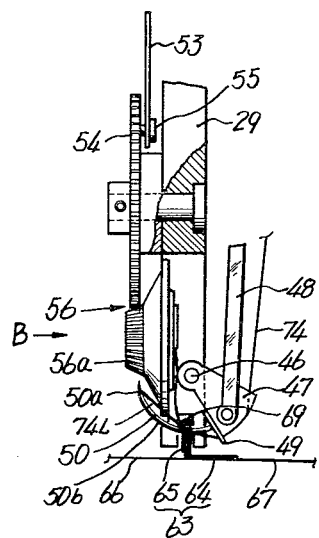

The solinoid 24 is made ON after T1 time and the solenoid 25 is made OFF. Then the cylinder rod 17c is lowered down to rotate the needle holder 47 around the pins 46 about 110° in the clockwise direction in FIG. 4, and the needle 50 penetrates into the dura maters 66, 67 till it comes to the position shown in FIG. 13. The pins 46, around which the needle holder 47 is rotated, are positioned at a center of a circle formed by rotation of the curved needle 50 so as to reduce the resistance of the dura maters 66, 67 against the penetration of the curved needle. The upper thread 74 is, on the outer periphery of the curved needle 50, given a tension owing to the friction with the thread guide 34 and the thread tension 49, and due to the tension at the thread tension 73. On the other hand, the upper thread is, on the side of inner periphery of the curved needle 50, exposed to the frictional resistance of the dura maters 66, 67 when the needle penetrates into the dura maters to be sutured. Therefore, in a condition that the needle 50 has been inserted into the dura maters with a maximum stroke as shown in FIG. 13, the upper thread 74 is, on the side of inner periphery of the curved needle 50, extended between the needle eye 50a and the dura maters 66, 67 to be stitched. As a result a crescent shaped loop 74L is formed as shown. In the surgical operation, where the thread is dipped into the adhesive blood or the humors, it can be easily unerstood that a suitable thread loop is not formed in the method by the conventional household sewing machine in which the thread loop is formed with the friction between the thread and the sewn fabric as the needle goes up after it comes to the lowest dead point. In this respect, the method of the present embodiment is preferable, in which the thread loop is formed as the curved needle 50 is inserted into the material to be sewn.

Figure 14:
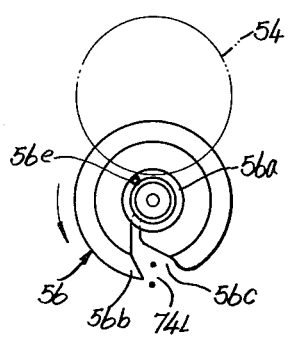
Figure 15:
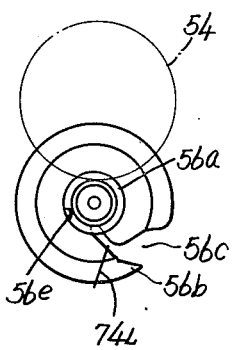
Figure 16:
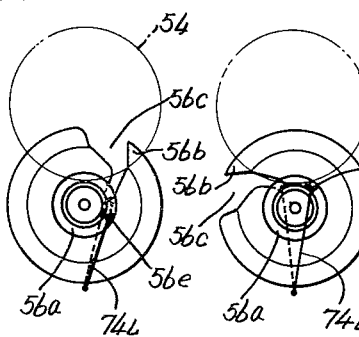
Figure 17:
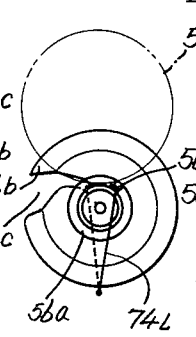
Figure 18:
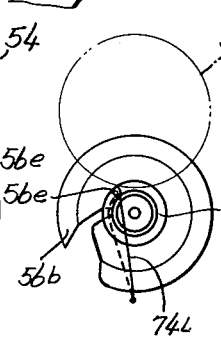
Figure 19:
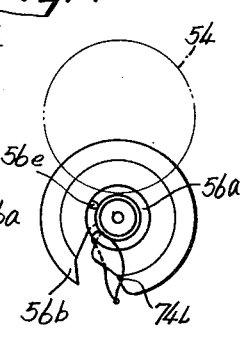

The solenoid 26 is made ON after T2 time, during which the needle 50 has been actuated, and the solenoid 27 is made OFF. Then the cylinder rod 18c is lowered to rotate the loop taker 56 about 340° in the present embodiment via the driving gear 54 and the gear 56a. In this process, the hook 56b of the loop taker 56 passes through the crescent loop 74L as shown in FIG. 13 or FIG. 14 and catches the loop 74L as shown in FIG. 15. As shown in FIGS. 16–19, as the loop taker 56 is rotated, the loop 74L is guided towards the center of the loop taker 56 along the cutout 56c, and is inserted into the groove 56e of the gear 56a (see FIG. 16). Since the groove 56e is deeper than the bottom of the gear, the loop 74L is guided past between the drive gear 54 and the gear 56a of the loop taker 56 without getting damage by the meshed gears 54, 56a, and is guided past around the lower thread bobbin 57 withing the loop taker 56, and is tied with the lower thread 59 (see FIG. 17 and FIG. 19). The groove 56e is extended obliquely across the gear 56a of the loop taker 56 as shown in FIG. 6, but the thread drawing is not limited to such type. The same effect may be obtained in a type of a spiral gear with a groove deeper than the bottom of the gear. It is well sufficient if the groove is designed to house and guide the tread 74 before the teeth of the two gears come to mesh around the groove with each other, and if the gear part of the loop taker is properly inclined to enable the thread to slide thereon. Further, instead of gears, friction wheels may be employed to drive the loop taker. In this case, the wheel of the loop taker is provided with a groove equivalent to the groove 56e of this embodiment for housing and guiding the thread 74, and is also properly inclined to enable the thread to slide thereon.

The solenoids 22, 24 are made OFF after T3 time, and the solenoid 25 is also made ON at the same time to retract the needle 50 and to lower the thread take-up element 33 to tighten the thread 74 to form a seam. The thread take-up element 33 pushes down the pin 37 of the feed regulator 36 and compresses the spring 38 by the predetermined amount so as to draw out a predetermined amount of the upper thread from the bobbin 70 for forming the next stitch, and at the same time to draw out a predetermined amount of the lower thread from the bobbin 57 in the loop taker 56 for the next stitch too.

The solenoid 27 is made ON after T4 time, and the silenoid 26 is made OFF, and simultaneously the solenoid 23 is made OFF at the same time. Then the loop taker 56 is rotated in the opposite direction for forming the next seam, and as the changing valve 19 is switched to the position of the center-open position due to the OFF of the solenoid 23, the rod side of the cylinder 16 and cylinder side become of the pressure equal to the atmospheric pressure. Therefore, the take-up element 33 is elevated by the amount predetermined by the feed regulator 36 owing to the biassing force of the spring 38 against the weight of the cylinder rod 16c itself and the friction thereof. As a result the thread 74 is given a sag for the next seam. In the above mentioned process, the sewing machine completes one cycle operation for forming one suturing seam. Then the operator displaces the sewing machine part 3 along the guide 64b, 65 of the presser foot 63, and the foot switch 15 is operated to form the next stitch. In this embodiment, the machine control part 2 and the suturing part 3 are connected with 6 flexible tubes 16a to 18b, and it is also possible to arrange, e.g., cams to be rotated by one cylinder on the suturing part 3 and actuate each of the mechanisms as keeping relation by means of said cams. In this case, if it is a doubleaction cylinder type, two flexible tubes are required, and if it is a single-action cylinder type, a single flexible tube is required.

According to this invention, due to the sag of the upper thread 74, the sewing machine part 3 can be lightly displaced for another stitch until the upper thread 74 is tensed. Therefore, the operator can easily form the stitches of a predetermined length without a special care. The stitch length may be varied by properly adjusting the feed regulator 36, namely by changing the sagging amount of the thread 74 which is determined by the amount of thread drawn out from the upper thread bobbin 70.

The times T1, T2, T3 and T4 are set longer thant the time needed to move the thread take-up element 30, the needle mechanism 31 and the loop taker mechanism 32. For example, if T1=150 ms (mm second), T2=250 ms, T3=500 ms and T4=350 ms. The total is 1250 ms. If the time is included to manually displace the sewing part 3, the time of, about 200 seconds is required to form 100 suturing seams in the ordinary craniotomy operation.

Figure 20:
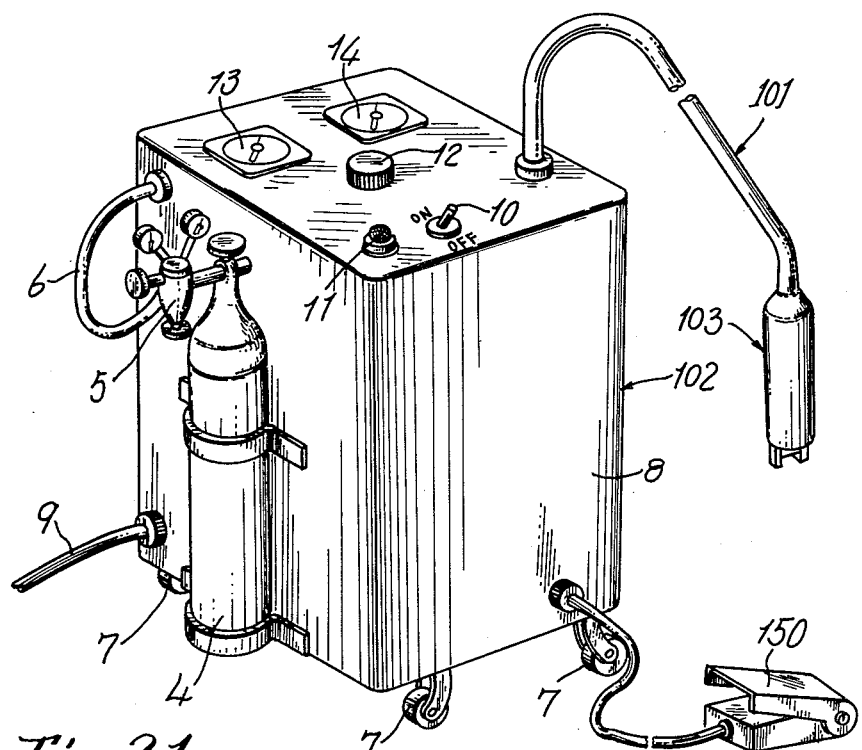
FIG. 20 is a perspective view of an outer appearance of a medical treating sewing machine.

A further reference will be made to a second embodiment of the invention. In FIG. 20, the numeral 101 designates a sewing machine for medical treatments composed of a controller 102 and a suturing part 103, which is different in the sttucture from the sewing machine in the first embosiment. The control part 102 is the same in principle as in the first embodiment, but different more or less. Since the remaining parts are the same, the same parts and places are given the same indicating numerals, but as cases require, those parts will be designated with different numerals.

Figure 21:
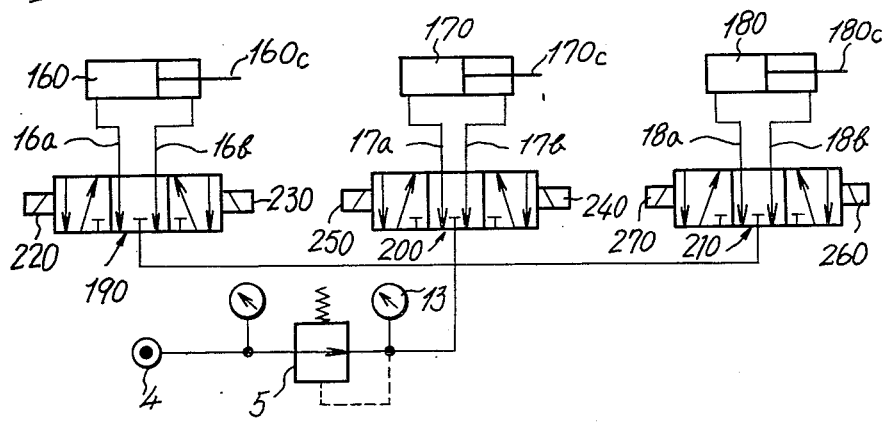
FIG. 21 is air-pressure circuit diagram.

In reference to FIG. 21, the numerals 160, 170 and 180 are double-acting cylinders of pressure fluid actuating devices, which are in this order connected to a $N_2$-gas high pressure bomb 4 via solenoid typed switching valves 190, 200 and 210. The numerals 220 to 270 are solenoids of said valves.

In reference to FIG. 22, there are, on a main body 104 of the part 103, provided cylinders 160, 170 and 180 for driving a take-up lever mechanism 105, a needle mechanism 106 and a looper mechanism 107, which are connected to solenoid typed switching valves 190, 200 and 210 housed in a box 8 of the control part 102 by a plurality of flexible tubes 16a to 18b, and are controlled by solenoids 220 to 270 which are sequentially controlled in an electric circuit (not shown) based on the same working principle as in the first embodiment. These flexible tubes 16a to 18b may be, if necessary, taken off from the top of the cylinders 160, 170 and 180. A cylinder rod 160c of the cylinder 160 is provided at its end with a take-up lever 108 formed with a thread eye 108a, which is vertically moving. The numeral 109 is a thread guide secured to the main body 104 with screws and formed with a thread guide hole 109a, which constructs the take-up lever mechanism 105 together with said take-up lever 108. The take-up lever 108 contacts a pin 37 of a feed controller 36 determining the feed amount at a lower end of its stroke and compresses a spring 38. With respect to the feed controller 36, the pin 37 is so inserted into a supporter 39 as to vertically move therein and is normally stopped by the biassing force of a spring 38 at a position where a stopper 40 stops under an upper part of the supporter 39. When the pin 37 is pushed down, the pin is moved while compressing the spring 38 until a nut 41 contacts an upper face of the supporter 39. Since the force of the spring 38 is determined such that it is weaker than working force of the cylinder 160 but stronger than the total of the friction resistance between the cylider rod 160c and sealing material and the own weight of said cylinder rod, the pin 37 is pushed down when the pressure fluid acts on the cylinder 160, and when this action is cancelled, the spring elevates the take-up lever 108 by the amount pushed down. This amount can be adjusted by changing the position of the nut 41.

In reference to FIG. 23, the cylinder rod 170c of the cylinder 170 is fixed with a needle coupling 110 at its end point, which is connected to a spur wheel 114 via a pin 111, a link 112 and a pin 113, and is fixed with a cam plate 115. The spur wheel meshes with another spur wheel 116 which is screwed to a bevel gear 117 to the body 104, which meshes with a bevel gear 120 integrally formed with a needle holder 120a pivoted to a bed plate 119. The numeral 50 is a curved needle secured to the needle holder 120a, and when the cylinder rod 170a elevates the curved needle 50 is rotated about 120° in this embodiment.

A cylinder rod 180c of the cylinder 180 is secured with a looper holder 121 fixing a looper 122, and these members constructs a looper mechanism. A control pin 123 which determines rotation direction of the looper 122 from the looper supporter 121, passes through a turned-over L shaped groove 124 and crosses with moving plain of the cam plate 115. The control pin 123 is biassed to the right in FIG. 22 by a coil spring 125 having an elongated leg, and is moved in a determined order within the groove 124 defined with longitudinal grooves 124a, 124b and an upper part 124c as mentioned later, by action of the coil spring 125, the cam plate 115 to be sequentially controlled and a cylinder rod 180c, in order to control the looper 122.

Figure 24:
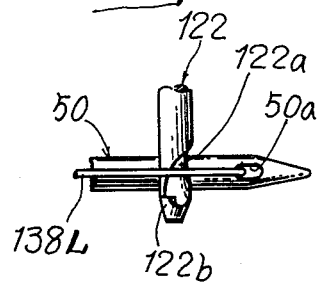
Figure 25:
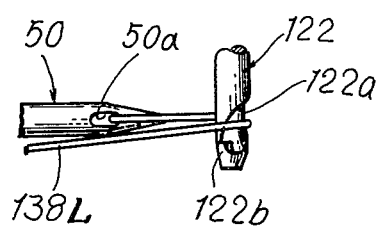
Figure 26:
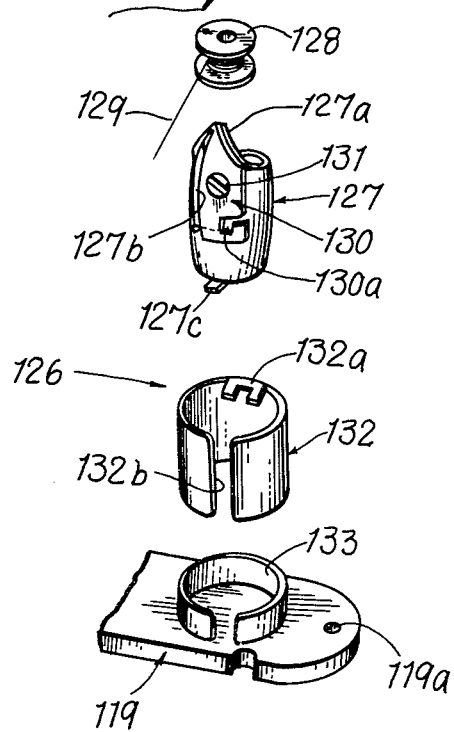
FIG. 26 is a perspective view of disembling the shuttle mechanism.
Figure 27:
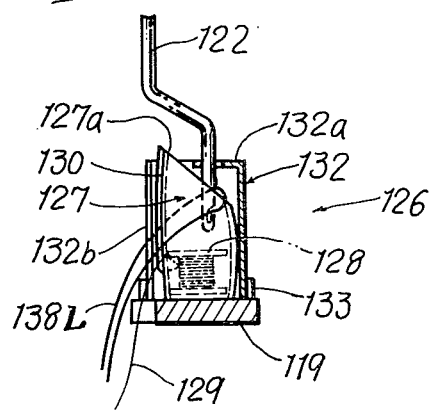
FIG. 27 is a cross sectional view showing relation between the shuttle mechanism and the looper.

In reference to FIG. 26, the numeral 126 is a shuttle mechanism positioned at a center of the curved needle 50, which constitutes a mechanism 142 providing the same effect as the racer together with the looper mechanism 107. The numeral 127 is a shuttle for housing a lower thread bobbin 128, and this shuttle is almost shaped in a cannon ball, formed with a pointed end 127a and a thread groove 127b for guiding a thread 129 of the lower thread bobbin 128 and having a plate spring 130 screwed by 131 for giving tension to the lower thread 129, and the shuttle is housed in a shuttle case 132. The numeral 130a is a thread supplying cutout formed in the plate spring 130. The numeral 127c is a positioning projection formed on the shuttle 127. The numeral 132a is a checking projection of the shuttle 127 formed on the shuttle case 132, and the numeral 132b is a slot. The numeral 133 is a holding metal for the shuttle case 132 fixed to the bed plate 119. The numeral 134 is a pressing plate (see FIG. 22) secured to the body 104 with a screw 135, which is composed of a connection 136 having spring property and a presser 137 which always presses the pointed head 127a of the shuttle 127 from a rear side. The looper 122 is, as shown in FIG. 25, with a spiral groove 122a starting at an opposing to a forward direction of the curved needle 50 and a hook 122b continuing to this groove 122a. Thus, the looper 122 catches the thread loop 138L as well as rotates in a counterclockwise direction seen from the upper parts in FIG. 24 and FIG. 25 so as to pass the thread loop to the shuttle 127. The numeral 139 is a guide fixed to the body 104, which is formed with a guiding groove 139a engaging the presser and an oblong groove 139b for inserting the needle. The numeral 140 is an upper thread bobbin, and 141 is a thread tension, these members being provided on an upper cover 143 of the suturing part 103. The upper cover 143 is detachably attached to the body 104, and a lower cover 144 is also detachably attached to the body with screws.

Actuation of the second embodiment constructed as mentioned above will be explained. As in the first embodiment, the dura maters are set to the presser before the suturing operation. The pressers are appropriately selected among prepared ones being different in size and shape in accordance with suturings, and two sheets of the dura maters are pressed with the pressers at the both sides and free ends of the presser are secured with forcepses. An upper end of the presser 63 set as mentioned is, as shown in FIG. 39, kept in a guiding groove 139a of the body 104 and the suturing is started. This operation is carried out by working a foot switch 150 and is stopped until one suturing is formed and the foot switch is worked secondly. The suturing is performed by repeating "operating the foot switch→forming one suturing and stopping the sewing machine→moving the sewing machine by the amount of feed pitch by manual operation." The lower cover can be taken off from the suturing part 103 by unscrewing, and in this condition the thread 138 passes, prior to the suturing, through the thread guide hole 119a of the bed plate 119 from the bobbin 140 provided on the upper cover 143 via the thread tension 141, the thread guide hole 104a, the take-up lever 108 and the thread guide 109, and the thread is guided to the oblong groove on the outer periphery of the curved needle 50 and passed through the needle eye 50a. After the upper thread 138 is set, the lower cover 144 can be easily provided on the part 103 in order reverse to the above mentioned.

Figure 28:
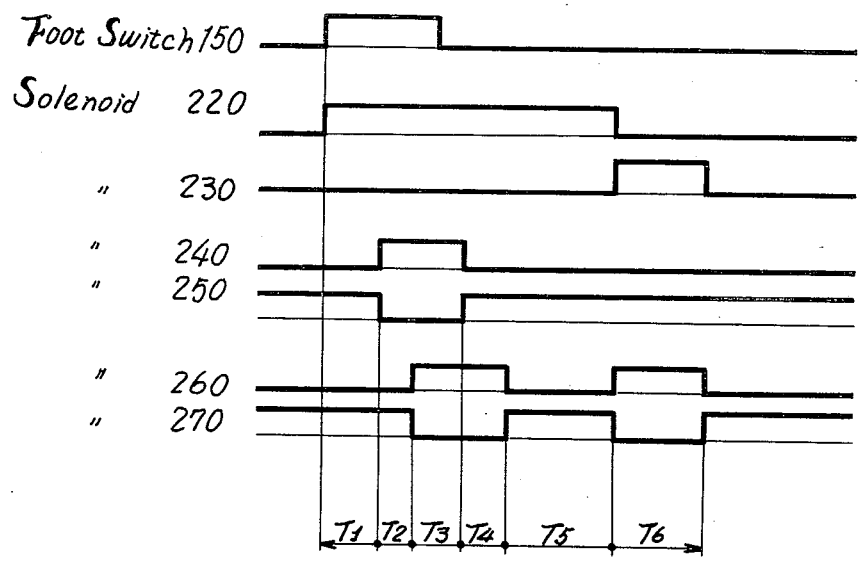
FIG. 28 is a sequence diagram of the solenoid.
Figure 29:
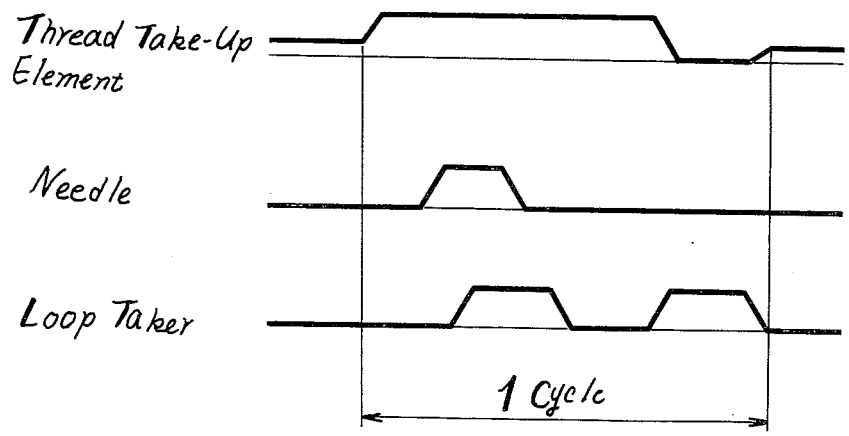
FIG. 29 is sequence of each of the mechanism of the suturing part.
Figure 42:
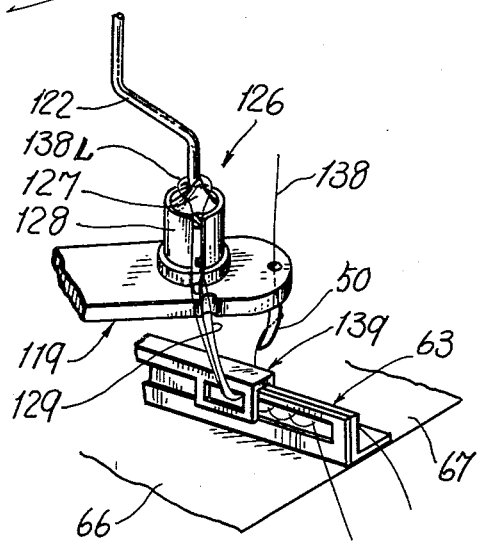
Figure 43:
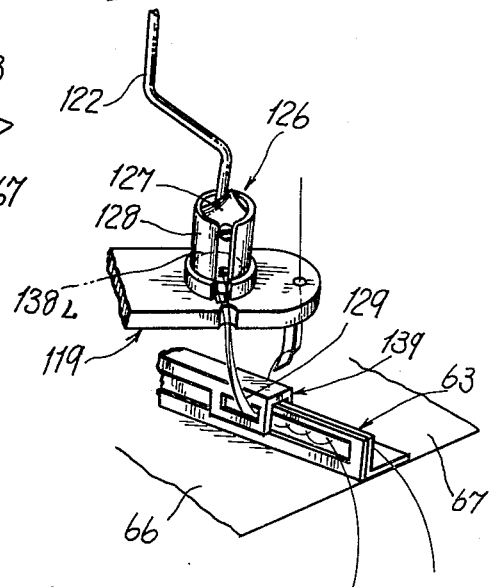
Figure 44:
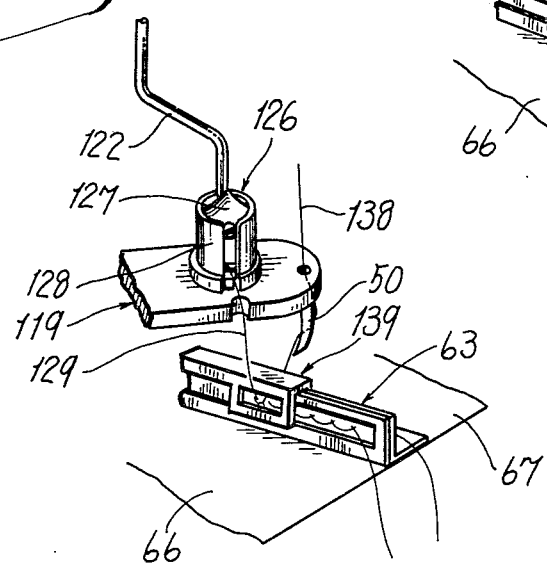

The suturing is formed by actuating each of the mechanisms in order shown in FIG. 29. These mechanisms are, as shown in FIG. 28, actuated by means of the switching valves 190, 200, 210 and the solenoids 220 to 270 which are sequentially controlled by the electric circuit (not shown) based on the same working principle as the first embodiment.

The initial condition prior to the suturing is apparent from the sequence in FIG. 11, and the cylinder rod 160c is in the center-open condition, the take-up lever 108 contacts at its lover face the pin 37 of the feed controller 36, the cylinder rod 170c is at the lowered position, and the cylinder rod 180c is at the elevated position.

When the foot switch 150 is operated by the foot from the above condition, the solenoid 220 is made ON and the N₂-gas flows into the rod sides of the cylinder 160 via the switching valve 190 so that the take-up lever 108 is elevated to give to the thread 138 the sag required to one suturing.

The solenoid 240 is made OFF after T1 time, and the solenoid 250 is made ON. The cylinder rod 170c elevates thereby the needle coupling 110 to rotate the needle 50 of the needle holder 120a about 120° around a pivot point via the link 112, the spur wheel 114, the spur wheel 116, the bevel gear 117 and the other bevel gear 120, so that the needle 50 passes through the dura mater to the position shown in FIG. 39. The pivot around which the needle holder 120a is rotated is positioned at a center which is formed by the curved needle 50 so that the resistance to penetration of the curved needle is reduced and the dura maters 66, 67 are avoided at the minimum in hurting. The upper thread 138 is given tension owing to the friction of the thread guide, and in a condition that the needle 50 works till the lower dead point shown in FIG. 39 the upper thread 138 is tensed between the needle eye 50a at the end point of the needle 50 and the penetrated hole of the affected part of the human person, and a crescent loop 138L is formed between the parts guided by the oblong groove 50b. Concurrently, the cam plate 115 fixed to the needle coupling 110 elevates from the condition shown in FIG. 30, and FIG. 31 to the condition in FIG. 32, and the control pin 123 of the looper holder 121 is pushed aside by the cam plate 115 at the upper part 124c of the groove 124 and is moved against the biassing force of the spring 125 to effect the directional control on the looper 122 (see FIG. 33).

The solenoid 260 is made ON after T2 time that the looper 122 is effected with the directional control and the solenoid 270 is made OFF and the cylinder rod 180c lowers the looper 122 as shown in FIG. 34 in a condition that the control pin 123 is guided to the oblong groove 124a, and causes the looper 122 to go into the crescent loop 138L.

Tthe solenoid 240 is made ON after T3 time and the solenoid 250 is made OFF, and the needle 50 retreats by lowering of the cylinder rod 170c in a condition that the thread loop 138L is given to the looper 122, and at the same time the cam plate 115 lowers (see FIG. 35 and FIG. 40).

The solenoid 260 is made OFF after T4 time, and the solenoid 270 is made ON, and the looper 122 elevates in a condition that the control pin 123 is guided to the oblong hole 124a, and pulls up the thread loop 138L while absorbing the sag of the thread by the take-up lever 108. The looper is biassed by the coil spring 125 at the highest position thereof and is rotated around the cylinder rod 180c by moving the control pin 123 in the upper part of the groove 124 (see FIG. 36, FIG. 37 and FIG. 41).

The solenoids 220, 270 are made OFF after T5 time and the solenoids 230, 260 are made ON. The looper goes down by the cylinder rod 180c in a condition that the control pin 123 is guided to the groove 124b, and the thread loop 138L is given to the shuttle 127 and at the same time the take-up lever 108 goes down by the cylinder rod 160c to begin tension of the thread. The thread loop 138L given to the shuttle 127 passes the shuttle as being wrung, to enable to knot the lower thread 129 and form suturings (see FIG. 37, FIG. 38 and FIGS. 42 to 44). The pointed head 127a of the shuttle 127 is not easily positioned at one position owing to such as touching of the upper thread when giving the looper 122 to the shuttle 127, however, in this embodiment since the head 127a is pushed by the pressing member 134 from its rear side, instability of positioning may be avoided.

The solenoid 230 is made OFF after T6 time, and since the switching valve 190 controlling the cylinder 160 is changed to the center open, the rod sides of the cylinder 160 and the cylinder sides become equal to the atmospheric pressure and the take-up lever 108 is elevated by length determined by the feed controller 36, by the biassing force of the spring 38 is given the sag. The solenoid 260 is made OFF at the same time as OFF of the solenoid 138 and the solenoid 270 is made ON. The cylinder rod 180c elevates the looper 122 and the control pin 123 returns to the initial condition shown in FIG. 30 by the force of the coil spring 125 and the looper 122 is thereby returned to the initial condition.

Until the above mentioned operation, the sewing machine completes on cycle operation for forming one suturing. The operator moves the suturing part 103 of the sewing machine along the pressure 63 and forms a next suturing by operating the foot switch 150. For moving the suturing part 103, the thread is in advance given the sag by the feed controller 36, and therefore the feed amount is almost constant, Also in this second embodiment, it is possible to compactly construct the suturing part as in the first embodiment and use the both hands of the operator to the operation of the sewing machine. Further the setting of the upper thread 138 before the operation, the washing and disinfection after the operation may be easily carried out. Since the $N_2$-gas is used as the fluid, no bad influence is given to the patient as in the first embodiment, and noise at the operation is very little generated.

As in the first embodiment and also in this embodiment, a little alternation is made to the suturing part 103 so that 6 flexible tubes can be changed to two or one.

It will be understood that each of the elements described above, or two or more together, may also find a useful application in other types of suturing machines differing from the types described above.

While the invention has been illustrated and described as embodied in a suturing instrument, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A suturing machine for surgical operations, comprising a suturing instrument; a control device; means for clamping the edges of the human parts to be sewn up, said suturing instrument having a needle carrying a thread, said clamping means including guide means for guiding the suturing instrument thereon along the parts to be sewn up, said suturing instrument including a base, a needle holder turnably mounted on said base, the needle being secured to the needle holder, a loop taker having a hook and turnably mounted on the base and operative for catching a thread loop formed on the needle, means to supply a predetermined amount of the thread to the needle, first transmission means adapted for reciprocating movement relative to the human parts to be sewn up and connected to the needle holder, second transmission means adapted for reciprocating movement relative to the human parts to be sewn up and connected to said loop taker, and third transmission means adapted for reciprocating movement relative to the human parts to be sewn up and connected to said supply means; said base of the suturing instrument being formed with groove means which are adaped to engage with the guide means of the clamping means so as to move the suturing instrument along the human parts clamped in the clamping means during the suturing operation; said control device including a fluid source, switching means operatively connected thereto and electric circuit means controlling said switching means; a plurality of hydraulic cylinders connected to said fluid switching means and each having a rod reciprocable in a respective cylinder, each respective rod being connected to the first transmission means, second transmission means and third transmission means, respectively; and a manually operated switch for activating said electric circuit means which sequentually operate said switching means which cause the sequential movement of the respective rods relative to the assigned cylinders to sequentially operate said first, second and third transmission means which respectively operate the needle so that it penetrates the human parts clamped in said clamping means, the loop taker catching the thread loop from the needle and the thread supply means supplying the thread to the needle to form up a suturing seam in the human parts to be sewn up while the suturing instrument is guided on the guide means along the human parts clamped in the clamping means.

2. The machine as defined in claim 1, wherein said clamping means further include a presser comprising two presser plates for holding the edges of the human parts to be sewn up and formed with an elongated opening through which the needle is inserted form a thread loop.

3. The machine as defined in claim 2, wherein said two presser plates are hingedly connected to each other.

4. The machine as defined in claim 1, wherein said switching means include a plurality of switching valves, each assigned to the respective cylinder.

5. The machine as defined in claim 4, wherein each of said switching valves includes two solenoids controlled by said electric circuit means and connecting said fluid source to the respective cylinder in response to a signal received from the electric circuit means.

6. The machine as defined in claim 5, wherein said base is formed with a first guide groove and a second guide groove, said first transmission means being guided in said first groove in its reciprocating movement, said second transmission means being also guided in said first groove in its reciprocating movement and said third transmission means being guided in said second guide groove in its reciprocating movement.

* * * * *